| United States Patent [19] | [11] Patent Number: 4,996,235 |
| --- | --- |
| Robertson et al. | [45] Date of Patent: Feb. 26, 1991 |

[54] 3,4-DIPHENYLBUTANAMINES

[75] Inventors: David W. Robertson, Greenwood; David T. Wong, Indianapolis, both of Ind.

[73] Assignee: Eli Lilly and Company, Indianapolis, Ind.

[21] Appl. No.: 125,512

[22] Filed: Nov. 25, 1987

[51] Int. Cl.⁵ .................. A61K 31/135; C07C 211/00
[52] U.S. Cl. .................... 514/649; 514/648; 514/656; 514/811; 564/315; 564/316; 564/373; 564/374; 564/378; 564/387
[58] Field of Search ............... 564/315, 316, 373, 374, 564/378, 387; 514/642, 649, 656

[56] References Cited

U.S. PATENT DOCUMENTS

| | | | |
| --- | --- | --- | --- |
| 3,079,403 | 2/1963 | Weinstock | 564/347 X |
| 3,138,639 | 6/1964 | Brossi et al. | 564/373 |
| 3,178,477 | 4/1965 | Seeger et al. | 564/373 |
| 3,308,157 | 3/1967 | Robertson et al. | 564/378 X |
| 3,328,249 | 6/1967 | Aceto et al. | 564/316 X |
| 3,689,504 | 9/1972 | Horrom | 564/378 X |
| 3,814,750 | 6/1974 | Cross et al. | 260/239 B |
| 3,928,369 | 12/1975 | Bernhard et al. | 564/316 X |
| 3,972,935 | 8/1976 | Molloy | 564/316 |
| 4,018,895 | 4/1977 | Molloy et al. | 424/330 |
| 4,034,011 | 7/1977 | Molloy | 564/316 |
| 4,062,955 | 12/1977 | Burn et al. | 564/387 X |
| 4,083,997 | 4/1978 | Houlihan et al. | 424/316 |
| 4,098,890 | 7/1978 | Molloy | 514/821 X |
| 4,194,009 | 3/1980 | Molloy et al. | 424/330 |
| 4,314,081 | 2/1982 | Molloy et al. | 564/347 |
| 4,329,356 | 5/1982 | Holland | 424/274 |
| 4,686,309 | 8/1987 | Barriere et al. | 564/355 |

FOREIGN PATENT DOCUMENTS

| | | | |
| --- | --- | --- | --- |
| 624117 | 5/1949 | United Kingdom | 564/319 |
| 2060618 | 5/1981 | United Kingdom . | |

OTHER PUBLICATIONS

Adamson et al., "Journal Chemical Society London", 1951, pp. 52–60.

Wolff, "Burger's Medicinal Chemistry", Part III, 4th Ed., pp. 1008, 1014–1017, 1038–1039 and 1041–1043 (1981).

Clark et al., *Journal of Medicinal Chemistry*, 22(11), 1373 (1979).

*Chemical Abstracts*, 79, 39056d (1973).

*Primary Examiner*—Robert V. Hines
*Attorney, Agent, or Firm*—Douglas J. Taylor; Leroy Whitaker

[57] ABSTRACT

The present invention provides 3,4-diphenylbutanamines capable of selectively inhibiting the uptake of serotonin and norepinephrine.

32 Claims, No Drawings

3,4-DIPHENYLBUTANAMINES

BACKGROUND OF THE INVENTION

U.S. Pat. Nos. 4,018,895, 4,194,009, and 4,314,081 disclose 3-aryloxy-3-phenylpropanamines as being potent, selective, blockers of the uptake of certain monoamines. For example, the hydrochloride salt of fluoxetine (dl-N-methyl-γ-[4-(trifluoromethyl)-phenoxy]benzenepropanamine) is a selective serotonin (5-hydroxytryptamine) uptake inhibitor useful in the treatment of depression, anxiety, obesity, and other disorders. Similarly, tomoxetine hydrochloride ((-)-N-methyl-γ-(2-methylphenoxy)benzenepropanamine hydrochloride) is a selective inhibitor of norepinephrine uptake currently undergoing clinical investigation for anti-depressant activity.

An object of this invention is to provide 3,4-diphenylbutanamines which are also potent, selective inhibitors of both serotonin and norepinephrine uptake.

SUMMARY OF THE INVENTION

The present invention provides 3,4-diphenylbutanamines which are potent, selective, serotonin and norepinephrine uptake inhibitors. More specifically, present invention relates to a compound of the formula

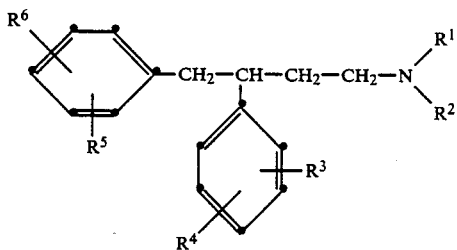

wherein:
$R^1$ and $R^2$ are each independently hydrogen or methyl;
$R^3$, $R^4$, $R^5$, and $R^6$ are each independently hydrogen, halo, trifluoromethyl, $C_1$–$C_4$ alkyl, $C_1$–$C_3$ alkoxy or $C_2$–$C_4$ alkenyl; or
a pharmaceutically acceptable acid addition salt thereof.

The invention also provides pharmaceutical formulations comprising a compound of the above formula and a pharmaceutically acceptable carrier, diluent, or excipient therefor. Further embodiments of the invention are methods for selectively inhibiting the uptake of serotonin and norepinephrine, as well as for treating a variety of disorders which have been linked to decreased neurotransmission of serotonin and norepinephrine in mammals including obesity, depression, alcoholism, pain, loss of memory, anxiety, smoking, and the like, employing a compound of the invention.

DETAILED DESCRIPTION OF THE INVENTION

In the above formula, the term "$C_1$–$C_4$ alkyl" represents a straight or branched alkyl chain bearing from one to four carbon atoms. Typical $C_1$–$C_4$ alkyl groups include methyl, ethyl, n-propyl, isopropyl, n-butyl, isobutyl, sec-butyl, and t-butyl. The term "$C_1$–$C_3$ alkoxy" represents methoxy, ethoxy, propoxy, or isopropoxy. The term "$C_2$–$C_4$ alkenyl" represents ethylene, propylene, isopropylene, 1-butene and 2-butene. Finally, the term "halo" represents chloro, fluoro, bromo, or iodo.

While all of the compounds of the present invention are believed to inhibit the uptake of serotonin and norepinephrine in mammals, certain of these compounds are preferred for such uses. Preferred compounds of the invention are those wherein $R^1$ is methyl, $R^2$, $R^3$, $R^4$, and $R^5$ are each hydrogen, and $R^6$ is either trifluoromethyl, $C_1$–$C_4$ alkyl, or $C_1$–$C_3$ alkoxy. Especially preferred compounds of the present invention are those wherein $R^1$, $R^2$, $R^3$, $R^4$, and $R^5$ are as above and $R^6$ is either methyl or trifluoromethyl. The most preferred compounds of the invention are N-methyl-3-phenyl-4-(4-trifluoromethylphenyl)butanamine and N-methyl-3-phenyl-4-(2-methylphenyl)butanamine.

The compounds of the present invention possess an asymmetric carbon atom represented by the carbon atom labeled "C" in the following formula

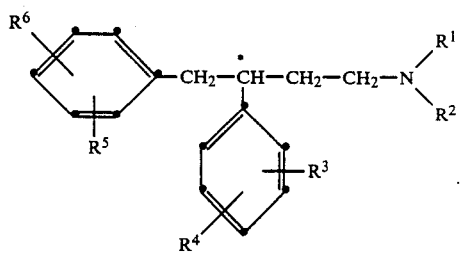

As such, the compounds can exist as individual stereoisomers as well as a racemic mixture. Accordingly, the compounds of the present invention include not only the racemates, but also their respective optically active d- and l-isomers. Unless otherwise indicated all compounds named herein are intended to exist as racemic mixtures.

The invention also includes pharmaceutically acceptable acid addition salts of the compounds defined by the above formula. Since the compounds of this invention are amines, they are basic in nature and accordingly react with any number of inorganic and organic acids to form pharmaceutically acceptable acid addition salts. Since the free amines of the invention are typically oils at room temperature, it is preferable to convert the free amines to their corresponding pharmaceutically acceptable acid addition salts, which are routinely solid at room temperature, for ease of handling. Acids commonly employed to form such salts include inorganic acids such as hydrochloric, hydrobromic, hydroiodic, sulfuric and phosphoric acid, as well as organic acids such as para-toluenesulfonic, methanesulfonic, oxalic, para-bromophenylsulfonic, carbonic, succinic, citric, benzoic, acetic, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, hydrochloride, hydrobromide, hydroiodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, p-toluenesulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such as oxalic acid, maleic acid, and para-toluenesulfonic acid.

The following compounds further illustrate compounds contemplated within the scope of the present invention:

N-methyl-3-phenyl-4-(4-trifluoromethylphenyl)-butanamine
  N-methyl-3-phenyl-4-(2-trifluoromethylphenyl)-butanamine
  N-methyl-3-phenyl-4-(3-trifluoromethylphenyl)-butanamine
  N-methyl-3-phenyl-4-(2-methylphenyl)butanamine
  N-methyl-3-phenyl-4-(3-methylphenyl)butanamine
  N-methyl-3-phenyl-4-(4-methylphenyl)butanamine
  N-methyl-3-phenyl-4-(2-ethylphenyl)butanamine
  N-methyl-3-phenyl-4-(4-ethylphenyl)-butanamine
  N-methyl-3-phenyl-4-(3-n-propylphenyl)-butanamine
  N-methyl-3-phenyl-4-(4-n-propylphenyl)-butanamine
  N-methyl-3-phenyl-4-(2-isopropylphenyl)-butanamine
  N-methyl-3-phenyl-4-(3-isopropylphenyl)-butanamine
  N-methyl-3-phenyl-4-(2-n-butylphenyl)-butanamine
  N-methyl-3-phenyl-4-(4-t-butylphenyl)-butanamine
  N-methyl-3-phenyl-4-(3-sec-butylphenyl)-butanamine
  N-methyl-3-phenyl-4-(4-isobutylphenyl)-butanamine
  N-methyl-3-phenyl-4-(2-methoxyphenyl)-butanamine
  N-methyl-3-phenyl-4-(3-methoxyphenyl)-butanamine
  N-methyl-3-phenyl-4-(4-methoxyphenyl)-butanamine
  N-methyl-3-phenyl-4-(2-ethoxyphenyl)-butanamine
  N-methyl-3-phenyl-4-(3-ethoxyphenyl)-butanamine
  N-methyl-3-phenyl-4-(3-n-propoxyphenyl)-butanamine
  N-methyl-3-phenyl-4-(4-isopropoxyphenyl)-butanamine
  N-methyl-3-phenyl-4-(2-chlorophenyl)-butanamine
  N-methyl-3-phenyl-4-(4-chlorophenyl)-butanamine
  N-methyl-3-phenyl-4-(3-fluorophenyl)-butanamine
  N-methyl-3-phenyl-4-(4-fluorophenyl)-butanamine
  N-methyl-3-phenyl-4-(3-bromophenyl)-butanamine
  N-methyl-3-phenyl-4-(2-iodophenyl)butanamine
  N-methyl-3-phenyl-4-(2-methyl-4-trifluoromethylphenyl)butanamine
  N-methyl-3-phenyl-4-(3-ethyl-2-methylphenyl)-butanamine
  N-methyl-3-phenyl-4-(5-ethoxy-2-isopropylphenyl)-butanamine
  N-methyl-3-phenyl-4-(2-methoxy-3-trifluoromethylphenyl)butanamine
  N-methyl-3-phenyl-4-(2,6-dichlorophenyl)-butanamine
  N-methyl-3-phenyl-4-(3-chloro-4-fluorophenyl)-butanamine
  N-methyl-3-phenyl-4-(3,5-difluorophenyl)-butanamine
  N-methyl-3-phenyl-4-(3-chloro-2-ethylphenyl)-butanamine
  N-methyl-3-phenyl-4-(2-bromo-5-trifluoromethylphenyl)butanamine
  N-methyl-3-phenyl-4-(2-fluoro-6-isopropoxyphenyl)-butanamine
  N-methyl-3-(2-methylphenyl)-4-(2-methylphenyl)-butanamine
  N-methyl-3-(4-ethylphenyl)-4-(4-trifluoromethylphenyl)butanamine
  N-methyl-3-(3-isopropoxyphenyl)-4-(3-chlorophenyl)butanamine
  N-methyl-3- 2-methoxyphenyl)-4-(2-trifluoromethylphenyl)butanamine
  N-methyl-3-(3-trifluoromethylphenyl)-4-(4-bromophenyl)butanamine
  N-methyl-3-(4-sec-butylphenyl)-4-(2-methoxyphenyl)butanamine
  N-methyl-3-(4-iodophenyl)-4-(3-propoxyphenyl)-butanamine
  N-methyl-3-(2-chlorophenyl)-4-(4-fluorophenyl)-butanamine
  N-methyl-3-(2-methylphenyl)-4-(5-chloro-2-methoxyphenyl)butanamine
  N-methyl-3-(4-trifluoromethylphenyl)-4-(2-ethyl-6-isopropoxyphenyl)butanamine
  N-methyl-3-(3-ethoxyphenyl)-4-(2-fluoro-5-t-butylphenyl)butanamine
  N-methyl-3-(2-bromophenyl)-4-(2,6-dimethylphenyl)butanamine
  N-methyl-3-(2,6-diethylphenyl)-4-(3,5-difluorophenyl)butanamine
  N-methyl-3-(5-isopropyl-2-methoxyphenyl)-4-(4-chloro-2-methylphenyl)butanamine
  N-methyl-3-(2,4-dichlorophenyl)-4-(2-chloro-5-fluorophenyl)butanamine
  N-methyl-3-(2-bromo-4-t-butylphenyl)-4-(2-ethoxy-6-sec-butylphenyl)butanamine
  N-methyl-3-(3-ethyl-5-methoxyphenyl)-4-phenyl-butanamine
  N-methyl-3-(4-trifluoromethylphenyl)-4-phenyl-butanamine
  N-methyl-3-(2-bromophenyl)-4-phenylbutanamine
  N-methyl-3-(2,6-dimethylphenyl)-4-phenylbutanamine
  N-methyl-3-phenyl-4-(3-ethylphenyl)butanaminium
  N-methyl-3-phenyl-4-(2-isobutylphenyl)-butanaminium sulfate
  N-methyl-3-phenyl-4-(2-n-propoxyphenyl)-butanaminium benzoate
  N-methyl-3-phenyl-4-(3-chlorophenyl)butanaminium tartrate
  N-methyl-3-phenyl-4-(2-bromophenyl)butanaminium lactate
  N-methyl-3-phenyl-4-(2-chloro-3-methoxyphenyl)-butanaminium phenylpropionate
  N-methyl-3-phenyl-4-(2,6-dimethylphenyl)-butanaminium glycollate
  N-methyl-3-(4-isopropylphenyl)-4-(2-methylphenyl)-butanaminium acetate
  N-methyl-3-(2-n-propoxyphenyl)-4-(3-ethyl-5-methylphenyl)butanaminium monohydrogen phosphate
  N-methyl-3-(2-chloro-3-trifluoromethylphenyl)--(2,6-dibromophenyl)butanaminium malonate
  N-methyl-3-(2-ethoxyphenyl)-4-phenylbutanaminium bisulfate
  N-methyl-3-(2-chloro-6-methylphenyl)-4-phenyl-butanaminium hydrobromide
  (+)-N-methyl-3-phenyl-4-(3-methylphenyl)-butanaminium fumarate
  (-)-N-methyl-3-(2-ethoxyphenyl)-4-(4-chlorophenyl)-butanaminium dinitrobenzoate (+)-N-methyl-3-(2-chloro-5-fluorophenyl)-4-phenyl-butanaminium decanoate
(-)-N-methyl-3-phenyl-4-(3,5-diisopropylphenyl)-butanaminium pyrophosphate
(+)-N-methyl-3-phenyl-4-(3-methoxyphenyl)-butanamine
(-)-N-methyl-3-(2-methyl-5-trifluoromethyl)-4-(2-ethoxyphenyl)butanamine
(+)-N-methyl-3-(4-methoxyphenyl)-4-phenylbutanamine
(-)-N-methyl-3-phenyl-4-(2,6-dibromophenyl)-butanamine
(+)-N-methyl-3-(2-ethoxy-4-methoxyphenyl)-4-(2-n-propylphenyl)butanamine
(-)-N-methyl-3-phenyl-4-(3-isopropylphenyl)-butanamine
N,N-dimethyl-3-phenyl-4-(4-trifluoromethylphenyl)-butanamine
N,N-dimethyl-3-phenyl-4-(2-trifluoromethylphenyl)-butanamine
N,N-dimethyl-3-phenyl-4-(3-trifluoromethylphenyl)-butanamine
N,N-dimethyl-3-phenyl-4-(2-methylphenyl)-butanamine
N,N-dimethyl-3-phenyl-4-(3-methylphenyl)-butanamine
N,N-dimethyl-3-phenyl-4-(4-methylphenyl)-butanamine
N,N-dimethyl-3-phenyl-4-(2-ethylphenyl)-butanamine
N,N-dimethyl-3-phenyl-4-(3-ethylphenyl)-butanamine
N,N-dimethyl-3-phenyl-4-(2-n-propylphenyl)-butanamine
N,N-dimethyl-3-phenyl-4-(4-n-propylphenyl)-butanamine
N,N-dimethyl-3-phenyl-4-(4-isopropylphenyl)-butanamine
N,N-dimethyl-3-phenyl-4-(3-isopropylphenyl)-butanamine
N,N-dimethyl-3-phenyl-4-(2-n-butylphenyl)-butanamine
N,N-dimethyl-3-phenyl-4-(3-n-butylphenyl)-butanamine
N,N-dimethyl-3-phenyl-4-(2-t-butylphenyl)-butanamine
N,N-dimethyl-3-phenyl-4-(4-sec-butylphenyl)-butanamine
N,N-dimethyl-3-phenyl-4-(3-isobutylphenyl)-butanamine
N,N-dimethyl-3-phenyl-4-(2-methoxyphenyl)-butanamine
N,N-dimethyl-3-phenyl-4-(3-methoxyphenyl)-butanamine
N,N-dimethyl-3-phenyl-4-(4-methoxyphenyl)-butanamine
N,N-dimethyl-3-phenyl-4-(4-ethoxyphenyl)-butanamine
N,N-dimethyl-3-phenyl-4-(3-ethoxyphenyl)-butanamine
N,N-dimethyl-3-phenyl-4-(2-n-propoxyphenyl)-butanamine
N,N-dimethyl-3-phenyl-4-(4-isopropoxyphenyl)-butanamine
N,N-dimethyl-3-phenyl-4-(2-chlorophenyl)-butanamine
N,N-dimethyl-3-phenyl-4-(3-chlorophenyl)-butanamine
N,N-dimethyl-3-phenyl-4-(2-fluorophenyl)-butanamine
N,N-dimethyl-3-phenyl-4-(4-fluorophenyl)-butanamine
N,N-dimethyl-3-phenyl-4-(2-bromophenyl)-butanamine
N,N-dimethyl-3-phenyl-4-(4-iodophenyl)-butanamine
N,N-dimethyl-3-phenyl-4-(3-ethoxy-4-trifluoromethylphenyl)butanamine
N,N-dimethyl-3-phenyl-4-(3-bromo-5-ethylphenyl)-butanamine
N,N-dimethyl-3-phenyl-4-(2-isopropyl-4-methoxyphenyl)butanamine
N,N-dimethyl-3-phenyl-4-(2-methyl-6-trifluoromethylphenyl)butanamine
N,N-dimethyl-3-phenyl-4-(2,4-diethylphenyl)-butanamine
N,N-dimethyl-3-phenyl-4-(3-chloro-4-n-propylphenyl)butanamine
N,N-dimethyl-3-phenyl-4-(2,6-dibromophenyl)-butanamine
N,N-dimethyl-3-phenyl-4-(2-fluoro-3-methylphenyl)-butanamine
N,N-dimethyl-3-phenyl-4-(2-chloro-5-trifluoromethylphenyl)butanamine
N,N-dimethyl-3-phenyl-4-(2-isopropoxy-3-fluorophenyl)butanamine
N,N-dimethyl-3-(2-methylphenyl)-4-(4-isopropylphenyl)butanamine
N,N-dimethyl-3-(3-ethylphenyl)-4-(4-trifluoromethylphenyl)butanamine
N,N-dimethyl-3-(3-ethoxyphenyl)-4-(2-iodophenyl)-butanamine
N,N-dimethyl-3-(4-n-propoxyphenyl)-4-(2-trifluoromethylphenyl)butanamine
N,N-dimethyl-3-(3-trifluoromethylphenyl)-4-(2-chlorophenyl)butanamine
N,N-dimethyl-3-(2-t-butylphenyl)-4-(2-methoxyphenyl)butanamine
N,N-dimethyl-3-(4-iodophenyl)-4-(4-methoxyphenyl)butanamine
N,N-dimethyl-3-(2-chlorophenyl)-4-(3-bromophenyl)butanamine
N,N-dimethyl-3-(3-ethylphenyl)-4-(3-fluoro-5-isopropoxyphenyl)butanamine
N,N-dimethyl-3-(4-trifluoromethylphenyl)-4-(2-ethyl-4-methoxyphenyl)butanamine
N,N-dimethyl-3-(2-ethoxyphenyl)-4-(2-chloro-5-t-butylphenyl)butanamine
N,N-dimethyl-3-(2-bromophenyl)-4-(2,4-di-n-propylphenyl)butanamine
N,N-dimethyl-3-(2,6-dimethylphenyl)-4-(3,4-dibromophenyl)butanamine
N,N-dimethyl-3-(2-ethoxy-6-sec-butylphenyl)-4-(2-ethyl-4-fluorophenyl)butanamine
N,N-dimethyl-3-(3,4-dichlorophenyl)-4-(2-bromo-3-fluorophenyl)butanamine
N,N-dimethyl-3-(2-fluoro-4-t-butylphenyl)-4-(2-ethoxy-6-methylphenyl)butanamine
N,N-dimethyl-3-(2-chloro-4-ethylphenyl)-4-phenyl-butanamine
N,N-dimethyl-3-(2-methoxy-6-trifluoromethylphenyl)-4-phenylbutanamine
N,N-dimethyl-3-(3-ethylphenyl)-4-phenylbutanamine
N,N-dimethyl-3-(2-methoxyphenyl)-4-phenylbutanamine N,N-dimethyl-3-phenyl-(2-methylphenyl)-butanaminium citrate N,N-dimethyl-3-phenyl-(3-n-propoxyphenyl)-butanaminium isobutyrate N,N-dimethyl-3-(2-trifluoromethylphenyl)-4-(2-fluoro-5-methylphenyl)butanaminium phenylacetate N,N-dimethyl-3-(2,6-difluoro)-4-phenyl-butanaminium maleate N,N-dimethyl-3-(3-bromophenyl)-4-phenyl-butanaminium hydroxybenzoate N,N-dimethyl-3-(3-isopropoxyphenyl)-4-(3-methylphenyl)butanaminium hydrochloride (+)-N,N-dimethyl-3-phenyl-4-(4-t-butylphenyl)-butanaminium succinate (+)-N,N-dimethyl-3-(2-chlorophenyl)-4-(3-trifluoromethylphenyl)butanaminium suberate (-)-N,N-dimethyl-3-(3,4-diethylphenyl)-4-phenyl-butanaminium carbonate (-)-N,N-dimethyl-3-(4-ethoxyphenyl)-4-(3-ethoxy5-methylphenyl)butanaminium mandelate (+)-N,N-dimethyl-3-phenyl-4-(2-methoxyphenyl)-butanamine (-)-N,N-dimethyl-3-(3-fluorophenyl)-4-phenylbutanamine (+)-N,N-dimethyl-3-(2-isopropoxy-6-methylphenyl)-4(2-bromo-4-chlorophenyl)butanamine (-)-N,N-dimethyl-3-(3-trifluoromethylphenyl)-4-(4-chlorophenyl)butanamine (+)-N,N-dimethyl-3-(2-n-propylphenyl)-4-phenyl-butanamine (-)-N,N-dimethyl-3-phenyl-4-(4-trifluoromethylphenyl)butanamine The compounds of the invention may be prepared according to the process shown in Reaction Scheme I below.

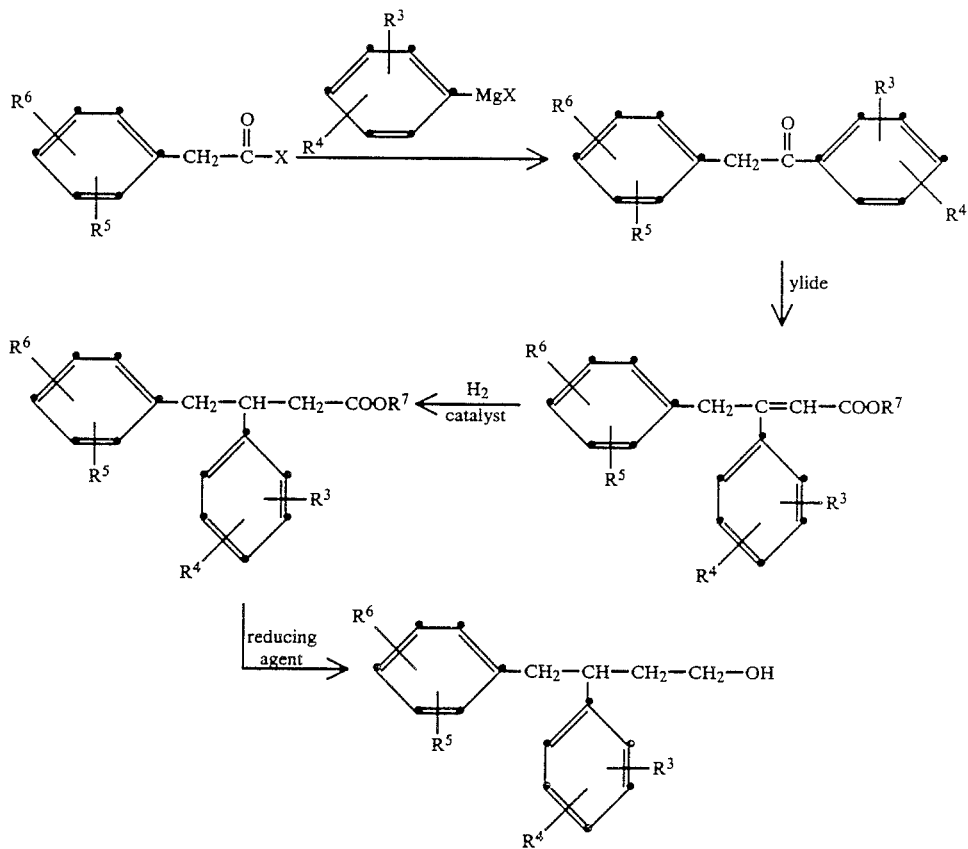

Reaction Scheme I

-continued
Reaction Scheme I

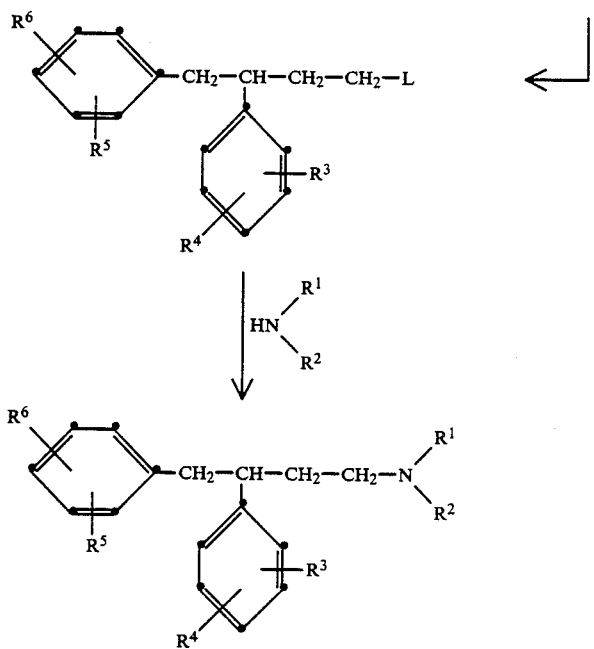

wherein $R^1$-$R^6$ are as defined previously;
X is halo;
$R^7$ is $C_1$-$C_4$ alkyl; and
L is a leaving group.

In the first step of the above process a suitably substituted phenylacetyl halide is reacted with a Grignard reagent, or some other suitable organometallic compound, to provide the corresponding 1,2-diphenylethanone. Grignard reagents suitable for preparing the ethanone include appropriately substituted phenylmagnesium halides such as phenylmagnesium chlorides, phenylmagnesium bromides, phenylmagnesium iodides, and the like. The Grignard reagent is preferably used in approximately equimolar quantities relative to the phenylacetyl halide in order to prevent further reaction of the ethanone to the corresponding alcohol. Suitable organometallic compounds include such compounds as appropriately substituted diphenylcadmiums, lithium diphenylcuprates, and the like. Unlike the Grignard reagents, these organometallic compounds can be used in greater than equimolar quantities relative to the phenylacetyl halide, if desired, since further reaction of the ethanone does not readily occur.

The above reaction is preferably conducted in a suitable inert solvent. Suitable inert solvents include the ethers such as diethyl ether, tetrahydrofuran and the like, or aromatic solvents such as benzene and the like. The reaction is substantially complete after about 5 minutes to about 6 hours when conducted at a temperature in the range of about $-100°$ C. to about $0°$ C. The ethanone product may be isolated, if desired, using standard isolation procedures. The isolated ethanone may be further purified, if desired, by standard techniques such as column chromatography over solid supports such as silica gel or alumina or crystallization from common solvents.

The ethanone is next reacted with an ylide employing known Wittig reaction conditions to provide an alkyl 3,4-diphenylbut-2-enoate. The ylide used in the reaction is most preferably prepared from a trialkylphosphonoacetate, such as triethylphosphonoacetate. However, ylides formed from (diphenylphosphinyl)acetic acid alkyl esters and phosphonium salts, such as (2-alkoxy-2-oxoethyl)triphenylphosphonium halides, tris(dimethylamino)(2-alkoxy-2-oxoethyl)phosphonium halides, and the like, can also be used. The ylide reactants are easily prepared by methods well known to one skilled in the art, preferably by reacting the phosphonoacetate or phosphonium salt with a base such as an alkyllithium or sodium hydride.

In general, the ethanone and ylide are reacted in approximately equimolar quantities. However, the amount of ylide used is not critical as long as at least an equimolar amount relative to the ethanone is used. The reaction is preferably conducted in a suitable nonreactive solvent such as an aromatic solvent, for example benzene and the like. The reaction is substantially complete after about one hour to about 48 hours when conducted at a temperature in the range of from about $25°$ C. to the reflux temperature of the reaction mixture. It is usually preferred to conduct the reaction at the reflux temperature of the reaction mixture since the reaction proceeds faster at the higher temperatures. The butenoate product may be isolated and purified, if desired, by standard techniques such as those discussed above.

The unsaturated double bond of the butenoate is next reduced using standard hydrogenation conditions to provide an alkyl 3,4-diphenylbutanoate. Standard hydrogenation conditions for preparing the butanoate involve the addition of hydrogen gas to a mixture of the butenoate and catalyst in an inert solvent. Suitable catalysts include platinum, nickel, copper chromite, palladium supported on a suitable inert surface such as carbon (Pd/C) or barium sulfate (Pd/BaSO$_4$), and the like. Acceptable inert solvents include alcohols such as methanol, ethanol, isopropanol and the like, and alkanoic acid solvents such as formic acid, acetic acid, isobutyric acid and the like. Preferred hydrogenation conditions involve the use of Pd/C and ethanol. The amount of catalyst required, reaction temperature, and reaction pressure are all variables which are within the ordinary skill of one versed in the art of organic chemistry. Once the reaction is substantially complete the butanoate is isolated by removing the catalyst by filtration and evaporating the inert solvent under reduced pressure.

The butanoate thus prepared is next reduced to provide a 3,4-diphenylbutanol. The reduction can be accomplished by several different methods. A preferred method uses reducing agents such as lithium aluminum hydride, lithium borohydride, or the like. Alternative methods for reducing the butanoate include the use of sodium in ethanol, or high temperature and pressure catalytic hydrogenation as hereinbefore described. The amount of reducing agent used, while not critical, is generally in the range of from about an equimolar amount relative to the butanoate to about two moles of reducing agent per mole of butanoate. The reaction is also preferably conducted in an inert solvent. Suitable inert solvents include ethers such as diethyl ether, tetrahydrofuran and the like, aromatic solvents such as benzene and the like, or alcohols such as methanol, ethanol, propanol and the like. The reaction is substantially complete after about 15 minutes to about 6 hours when conducted at temperatures in the range of about $-10°$ C. to about 50° C. The butanol thus prepared is isolated by quenching the reaction mixture with water, followed by isolation using standard isolation procedures.

The hydroxy group of the butanol thus prepared is next replaced with a leaving group such as p-toluenesulfonyl, methanesulfonyl, triphenylphosphine oxide, halo, and the like. A preferred leaving group is methanesulfonyl, which is readily provided by reacting the butanol with methanesulfonyl chloride in the presence of at least one molar equivalent of a suitable acid scavenger such as triethylamine or the like. Other leaving groups may be provided in a similar manner or by alternate methods well known to one skilled in the art. The butanol is reacted with from an equimolar quantity to a slight molar excess (about 20% by weight) of the compound which provides the leaving group The reaction is preferably conducted in a non-reactive solvent, for example in ethers such as diethyl ether and tetrahydrofuran, aromatic solvents such as benzene, or other related solvents. The reaction is substantially complete after about 10 minutes to about 12 hours when conducted at temperatures in the range of about 0° C. to about 50° C. The product may then be isolated, if desired, using standard isolation techniques.

Finally, the 3,4-diphenylbutanamines of the invention are provided by reacting the compound containing a leaving group with either methylamine (one of $R^1$ and $R^2$ is methyl and the other is H), dimethylamine ($R^1$ and $R^2$ are methyl), or ammonia ($R^1$ and $R^2$ are H). The amount of amine used is not critical so long as at least an equimolar amount relative to the amount of starting material is employed. However, it is often preferable to use a molar excess of the amine reactant in order to increase the rate of reaction.

The above reaction is preferably conducted in a suitable inert solvent, for instance in alcohols such as methanol, ethanol, isopropanol and the like, ethers such as diethyl ether, tetrahydrofuran and the like, and aromatic solvents such as benzene and the like. The reaction is substantially complete after about one hour to about 48 hours when conducted at a temperature in the range of from about 10° C. to about 75° C., more preferably from about 20° C. to about 50° C.

The product butanamine may be isolated using standard isolation techniques. Typically, the solution containing the butanamine is concentrated by removing the inert solvent by distillation. The resulting residue is then dissolved in a water immiscible organic solvent such as diethyl ether, ethyl acetate, chloroform and the like, and the resulting solution is washed with water and dried. Following evaporation of the organic solvent, the isolated residue may be further purified, if desired, by standard techniques such as crystallization from common solvents, or chromotography over solid supports such as silica gel or alumina.

Alternatively, the 3,4-diphenylbutanamines of the invention in which $R^1$ and $R^2$ are both hydrogen can be prepared by reacting the compound containing a leaving group with a large excess of ammonia in a high pressure reactor. This reaction may be run with or without a solvent. The reaction is substantially complete after about 6 hours to about 48 hours when conducted at a temperature in the range of about 75° C. to about 150° C. The product produced may be isolated as described above.

The compounds of the present invention wherein one of $R^1$ and $R^2$ is methyl and the other is hydrogen may alternatively be prepared by demethylating the corresponding N,N-dimethylbutanamine. Preferably, a reagent such as phenyl chloroformate, trichloroethyl chloroformate, or cyanogen bromide is reacted with the N,N-dimethylbutanamine to provide an intermediate, which is then hydrolyzed in a base to yield a compound of this invention in which one of $R^1$ and $R^2$ is methyl and the other is hydrogen.

As noted above, the optically active isomers of the racemates of the invention are also considered part of this invention. Such optically active isomers may be prepared from their respective optically active precursors by the procedures described above, or by resolving the racemic mixtures. This resolution can be carried out in the presence of a resolving agent, by chromatography or by repeated crystallization. Particularly useful resolving agents include dibenzoyl-d- and -l-tartaric acids and the like.

The pharmaceutically acceptable acid addition salts of the invention are typically formed by reacting a 3,4-diphenylbutanamine of the invention with an equimolar or excess amount of a pharmaceutically acceptable acid. The reactants generally are combined in a mutual solvent such as acetone, diethyl ether, or benzene. The salt normally precipitates out of solution within about one hour to 10 days, and can be isolated by filtration.

The starting materials employed in synthesizing the compounds of the invention; namely, the suitably substituted phenylacetyl halides and the appropriately substituted Grignard reagents or other organometallic compounds, are either commercially available, known in the literature, or can be prepared by methods known in the art.

The following Examples further illustrate the compounds of the present invention and methods for their synthesis. The Examples are not intended to be limiting to the scope of the invention in any respect and should not be so construed.

EXAMPLE 1

N-Methyl-3-phenyl-4-(4-trifluoromethylphenyl)-butanaminium chloride

To a 250 ml, round bottom flask fitted with a condenser were added 73.0 g (358 mmole) of p-trifluoromethylphenylacetic acid and 107 ml (1.5 mole) of thionyl chloride. The mixture was heated to reflux and stirred at that temperature for about 2½ hours. The condenser was removed and the unreacted thionyl chloride was evaporated by vacuum distillation to provide a slurry consisting essentially of p-trifluoromethylphenylacetyl chloride.

The phenylacetyl chloride was dissolved in 100 ml of tetrahydrofuran and the resulting solution was cooled to about −78° C. A solution of phenylmagnesium bromide (64.9 g, 358 mmole) dissolved in tetrahydrofuran (200 ml) was added dropwise to the cold phenylacetyl chloride solution over a period of 15 minutes. The reaction solution was stirred for an additional 30 minutes at a temperature of about −78° C. and water (200 ml) was added dropwise over a period of about 15 minutes. The resulting organic layer was separated, dried over anhydrous sodium sulfate, and concentrated under reduced pressure to provide a residue. The residue was purified by preparature high performance liquid chromatography (0–10% ethyl acetate in hexane gradient by volume) to afford 9.67 g (10.0% yield) of 1-phenyl-2-(4-trifluoromethylphenyl)ethanone as a white powder following evaporation of the organic solvent. A sample of the powder was further purified by recrystallization from ethyl acetate/-hexane for analytical characterization. mp=143°–144° C.

Analysis calculated for $C_{15}H_{11}F_3O$: Theory: C, 68.18; H, 4.20; Found: C, 68.41; H, 4.23.

Triethylphosphonoacetate (5.31 ml, 26.8 mmole) was added dropwise over a five minute period to a 250 ml flask containing a stirred mixture of sodium hydride (984.0 mg of a 60% by weight dispersion of sodium hydride in mineral oil, 24.6 mmole of sodium hydride) in 50 ml of benzene. After hydrogen evolution ceased, a solution of 5.65 g (21.4 mmole) of 1-phenyl-2-(4-trifluoromethylphenyl)ethanone dissolved in 100 ml of benzene was added. The reaction solution was stirred at reflux overnight and cooled to room temperature (22° C). The reaction solution was partitioned between ethyl acetate and water. The organic layer was separated, dried over anhydrous sodium sulfate, and concentrated under reduced pressure. Flash chromatography (silica gel; 0–5% ethyl acetate in hexane gradient by volume) afforded 4.24 g (59.0% yield) of ethyl 3-phenyl-4-(4-trifluoromethylphenyl)but-2(E,Z)-enoate as a clear oil. The compound was identified by N.M.R. analysis employing a 300 mHz instrument in $CDCl_3$: δ=1.25 and 1.30 (triplet, 3H); 3.64 and 4.56 (singlet, 2H); 4.10 and 4.23 (quintuplet, 2H); 6.48 and 7.00 (broad singlet, 1H); 7.24–7.66 (multiplet, 9H). The N.M.R. analysis further revealed that the product was 1:2:1 mixture of isomers.

The enoate isomers (5.19 g, 15.5 mmole) and 700 mg of 5% (weight %) palladium on carbon were suspended in 200 ml of ethanol. After degassing, the mixture was stirred in the presence of a 35 psig hydrogen atmosphere until the theoretical amount of hydrogen had been consumed. The reaction mixture was filtered through diatomaceous earth to remove the solids and concentrated under reduced pressure to yield 4.5 g (86.0% yield) of ethyl 3-phenyl-4-(4-trifluoromethylphenyl)butanoate as a clear oil. N.M.R. analysis employing a 300 mHz instrument in $CDCl_3$ provided: δ=1.12 (triplet, 3H); 2.6 (doublet, 2H); 2.98 (multiplet, 2H); 3.42 (multiplet, 1H); 4.01 (quintuplet, 2H); 7.06–7.51 (multiplet, 9H).

Analysis calculated for $C_{19}H_{19}F_3O_2$: Theory: C, 67.85; H, 5.69; Found: C, 67.76; H, 5.78.

A solution of 4.4 g (13.1 mmole) of ethyl 3-phenyl-4-(4-trifluoromethylphenyl)butanoate dissolved in 50 ml of tetrahydrofuran was added dropwise over a ten minute period to a 250 ml flask containing a 0° C. mixture of lithium aluminum hydride (745 mg, 19.6 mmole) in 50 ml of tetrahydrofuran. The resulting mixture was warmed to room temperature (22° C.), stirred at that temperature for about 2 hours, cooled to 0° C. again, and quenched by adding approximately 25 ml of water dropwise over a five minute period. The reaction mixture was acidified to a pH of about 1.0 using 6N hydrochloric acid and extracted with ethyl acetate. The organic extracts were combined, washed with water and a saturated brine solution, and finally dried over anhydrous sodium sulfate. The volatiles were removed under reduced pressure to provide 3.66 g of 3-phenyl-4-(4-trifluoromethylphenyl)butanol as a colorless oil. The compound was identified by N.M.R. analysis employing a 300 mHz instrument in $CDCl_3$; δ=1.92 (multiplet, 2H); 2.97 (multiplet, 3H); 3.43 and 3.52 (multiplet, 2H); 7.08–7.53 (multiplet, 9H).

3-Phenyl-4-(4-trifluoromethylphenyl)butanol (3.65 g, 12.4 mmole) was dissolved in 50 ml of tetrahydrofuran and the resulting solution was cooled to about 0° C. Triethylamine (1.82 ml, 13.0 mmole) was added, followed by the dropwise addition of 1.01 ml (13.0 mmole) of methanesulfonyl chloride over a five minute period. The solution was stirred at room temperature (22° C.) for about 2 hours. The reaction solution was then partitioned between ethyl acetate and water. The resulting organic layer was washed with a saturated brine solution, dried over anhydrous sodium sulfate, and then concentrated under reduced pressure to provide 4.47 g of 3-phenyl-4-(4-trifluoromethylphenyl)butane sulfonic acid methyl ester as a yellow oil. N.M.R. analysis (300 MHz instrument, in $CDCl_3$) provided: δ=1.98–2.25 (broad multiplet, 2H); 2.80 (singlet, 3H); 3.00 (multiplet, 3H); 3.92 and 4.09 (multiplet, 2H); 7.02–7.45 (multiplet, 9H).

Methylamine (37.2 ml of a 40% by weight aqueous solution, 481 mmole) was added to a 250 ml flask containing 4.47 g (12.0 mmole) of 3-phenyl-4-(4-trifluoromethylphenyl)butane sulfonic acid methyl ester dissolved in 50 ml of tetrahydrofuran. The resulting solution was stirred overnight at room temperature (22° C.) and concentrated under reduced pressure to provide a residue. The residue was dissolved in ethyl acetate and the resulting solution was washed with water and a saturated brine solution. The organic solution was dried over anhydrous sodium sulfate and the volatiles were removed under reduced pressure to provide 3.5 g of N-methyl-3-phenyl-4-(4-trifluoromethylphenyl)butanamine as an oil. A sample of the oil was crystallized from an acetone/diethyl ether solution containing 1.5 equivalents of concentrated hydrochloric acid to yield N-methyl-3-phenyl-4-(4-trifluoromethylphenyl)butanamine hydrochloride as white crystals. mp=156°–157.5° C.

Analysis calculated for $C_{18}H_{20}F_3N \cdot HCl$: Theory: C, 62.88; H, 6.16; N, 4.07; Found: C, 63.01; H, 6.30; N, 4.01.

EXAMPLE 2

N-Methyl-3-phenyl-4-(2-methylphenyl)-butanaminium tosylate

The title compound was prepared from 1-phenyl-2-(2-methylphenyl)ethanone according to the general procedure described in Example 1. The tosylate salt was prepared by using an acetone/diethyl ether solution containing 1.5 equivalents of p-toluenesulfonic acid. mp=94°-96° C.

Analysis calculated for $C_{18}H_{23}N \cdot C_7H_8O_3S$: Theory: C, 70.55; H, 7.34; N, 3.29; Found: C, 70.30; H, 7.45; N, 3.29.

As noted above, the compounds of this invention are useful for inhibiting the uptake of serotonin. Therefore, another embodiment of the present invention is a method for inhibiting serotonin uptake in mammals which comprises administering to a mammal requiring increased neurotransmission of serotonin a pharmaceutically effective amount of a compound of the invention.

Compounds of the invention also have the ability to inhibit the uptake of norepinephrine. As such, yet another embodiment of this invention is a method for inhibiting norepinephrine uptake in mammals which comprises administering to a mammal requiring increased neurotransmission of norepinephrine a pharmaceutically effective amount of a compound of the invention.

The term "pharmaceutically effective amount", as used herein, represents an amount of a compound of the invention which is capable o inhibiting serotonin or norepinephrine uptake. The particular dose of compound administered according to this invention will of course be determined by the particular circumstances surrounding the case, including the compound administered, the route of administration, the particular condition being treated, and similar considerations. The compounds can be administered by a variety of routes including the oral, rectal, transdermal, subcutaneous, intravenous, intramuscular or intranasal routes. It is a special feature of the compounds that they have good oral bioavailability without losing their substantial potent inhibiting effect on serotonin and norepinephrine uptake. A typical daily dose will contain from about 0.01 mg/kg to about 20 mg/kg of the active compound of this invention. Preferred daily doses will be about 0.05to about 10 mg/kg, ideally about 0.1 to about 5 mg/kg.

A variety of physiologic functions have been shown to be subject to influence by brain serotoninergic and norepinephrinergic neural systems. As such, the compounds of the present invention are believed to have the ability to treat a variety of disorders in mammals associated with these neural systems such as obesity, depression, alcoholism, pain, loss of memory, anxiety and smoking. Therefore, the present invention also provides methods of treating the above disorders at the rates set forth above for inhibiting serotonin and norepinephrine uptake in mammals.

The following experiment was conducted to demonstrate the ability of the compounds of the present invention to inhibit the uptake of serotonin and norepinephrine. This general procedure is set forth by Wong et al., in *Drug Development Research* 6:397–403 (1985).

Male Sprague-Dawley rats (110–150 g) from Harlan Industries (Cumberland, Ind.) were fed a Purina Chow ad libitum for at least 3 days before being used in the studies. Rats were killed by decapitation. Whole brains were removed and dissected. Cerebral cortex was homogenized in 9 volumes of a medium containing 0.32 M sucrose and 10 mM glucose. Crude synaptosomal preparations were isolated after differential centrifugation at 1,000 g for 10 min. and 17,000 g for 28 min. The final pellets were suspended in the same medium and kept in ice until use within the same day.

Synaptosomal uptake of $^3H$-serotonin($^3H$-5-hydroxytryptaine, $^3H$-5HT) and $^{14}C$-l-norepinephrine ($^{14}C$-NE) was determined as follows. Cortical synaptosomes (equivalent to 1 mg of protein) were incubated at 37° C. for 5 min in 1 ml of Krebs-bicarbonate medium containing also 10 mM glucose, 0.1 mM iproniazid, 1 mM ascorbic acid, 0.17 mM EDTA, 50 nM $^3H$-5HT and 100 nM $^{14}C$-NE. The reaction mixture was immediately diluted with 2 ml of ice-chilled Krebs-bicarbonate buffer and filtered under vacuum with a cell harvester (Brandel, Gaithersburg, Md.). Filters were rinsed twice with approximately 5 ml of ice-chilled 0.9% saline and were transferred to a counting vial containing 10 ml of scintillation fluid (PCS, Amersham, Arlington Heights, Ill.). Radioactivity was measured by a liquid scintillation spectrophotometer. Accumulation of $^3H$-5HT and $^{14}C$-NE at 4° C. represented the background and was subtracted from all samples.

While all of the compounds of the invention inhibit the uptake of serotonin and norepinephrine to some degree, certain of the compounds possess a unique selectivity in that they block the uptake of one of the monoamines to a far greater extent than they do the uptake of the other monoamine. The results of the evaluation of compounds of the present invention are set forth below in Table I. In the Table, columns 2–7 identify the structure of the compounds evaluated when taken with the formula set forth in the heading; column 8 identifies the salt form of the compound evaluated; and columns 9 and 10 provide the concentration of the test compound at $10^9 M$ (nM) needed to inhibit 50% of serotonin (5HT) or norepinephrine, respectively, and is indicated in the Table as $IC_{50}$.

TABLE I
INHIBITION OF 5HT AND NOREPHRINE UPTAKE IN VITRO

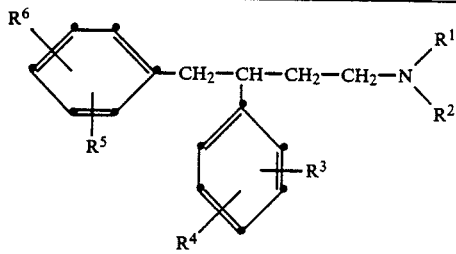

| Compound of Example No. | $R^1$ | $R^2$ | $R^3$ | $R^4$ | $R^5$ | $R^6$ | Salt Form | IC$_{50}$ (nM) 5HT | IC$_{50}$ (nM) NE |
|---|---|---|---|---|---|---|---|---|---|
| 1 | CH$_3$ | H | H | H | CF$_3$* | H | hydrochloride | 250 | 7600 |
| 2 | CH$_3$ | H | H | H | CH$_3$+ | H | tosylate | 330 | 100 |

*para position
+meta position

The compounds of the present invention are preferably formulated prior to administration. Therefore, yet another embodiment of the present invention is a pharmaceutical formulation comprising a compound of the invention and a pharmaceutically acceptable carrier, diluent or excipient therefor.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), ointments containing, for example, up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyland propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient by employing procedures well known in the art.

The compositions are preferably formulated in a unit dosage form, each dosage containing from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

FORMULATION 1

Hard gelatin capsules are prepared using the following ingredients:

| | Quantity (mg/capsule) |
|---|---|
| N-methyl-3-phenyl-4-(4-trifluoromethyl-phenyl)butanaminium hydrochloride | 250 |
| starch, dried | 200 |
| magnesium stearate | 10 |
| Total | 460 mg |

The above ingredients are mixed and filled into hard gelatin capsules in 460 mg quantities.

FORMULATION 2

A tablet is prepared using the ingredients below:

| | Quantity (mg/tablet) |
|---|---|
| N-methyl-3-phenyl-4-(2-methylphenyl)-butanaminium tosylate | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

FORMULATION 3

An aerosol solution is prepared containing the following components:

| | Weight % |
|---|---|
| (+)-N-methyl-3-phenyl-4-(2-methylphenyl)-butanaminium tosylate | 0.25 |
| ethanol | 29.75 |
| Propellant 22 (chlorodifluoromethane) | 70.00 |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

FORMULATION 4

Tablets each containing 60 mg of active ingredient are made as follows:

| | |
|---|---|
| (−)-N-methyl-3-phenyl-4-(4-trifluoromethyl-phenyl)butanaminium hydrochloride | 60 mg |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION 5

Capsules each containing 80 mg of medicament are made as follows:

| | |
|---|---|
| N-methyl-3-phenyl-4-(2-methylphenyl)-butanaminium tosylate | 80 mg |
| starch | 59 mg |
| microcrystalline cellulose | 59 mg |
| magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

FORMULATION 6

Suppositories each containing 225 mg of active ingredient may be made as follows:

| | |
|---|---|
| (+)-N-methyl-3-phenyl-4-(4-trifluoro-methylphenyl)butanaminium hydrochloride | 225 mg |
| saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions each containing 50 mg of medicament per 5 ml dose are made as follows:

| | |
|---|---|
| (−)-N-methyl-3-phenyl-4-(2-methylphenyl)-butanaminium tosylate | 50 mg |
| sodium carboxymethyl cellulose | 50 mg |
| syrup | 1.25 ml |
| benzoic acid solution | 0.10 ml |
| flavor | q.v. |
| color | q.v. |
| purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

FORMULATION 8

An intravenous formulation may be prepared as follows:

| | |
|---|---|
| N-methyl-3-phenyl-4-(2-methylphenyl)-butanaminium tosylate | 100 mg |
| isotonic saline | 1000 ml |

The solution of the above ingredients is administered intravenously at a rate of 1 ml per minute to a subject suffering from depression.

We claim:

1. A compound of the formula

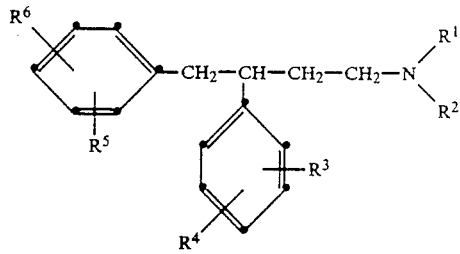

wherein:

$R^1$ and $R^2$ are each independently hydrogen or methyl;

$R^3$, $R^4$, $R^5$, and $R^6$ are each independently hydrogen, halo, trifluoromethyl, $C_1$–$C_4$ alkyl, $_1$–$C_3$ alkoxy or $C_2$–$C_4$ alkenyl; or a pharmaceutically acceptable acid addition salt thereof.

2. A compound of claim 1 wherein $R^1$ is methyl, $R^2$, $R^3$, $R^4$, and $R^5$ are each hydrogen, and $R^6$ is trifluoromethyl, $C_1$–$C_4$ alkyl or $C_1$–$C_3$ alkoxy.

3. A compound of claim 2 wherein $R^6$ is either trifluoromethyl or methyl.

4. A compound of claim 3, said compound being N-methyl-3-phenyl-4-(4-trifluoromethylphenyl)butanamine, or a pharmaceutically acceptable acid addition salt thereof.

5. A compound of claim 3, said compound being N-methyl-3-phenyl-4-(2-methylphenyl)butanamine, or a pharmaceutically acceptable acid addition salt thereof.

6. A method for inhibiting serotonin uptake in mammals which comprises administering to a mammal requiring increased neurotransmission of serotonin a pharmaceutically effective amount of a compound of claim 1.

7. A method of claim 6 wherein $R^1$ is methyl, $R^2$, $R^3$, $R^4$, and $R^5$ are each hydrogen, and $R^6$ is either trifluoromethyl, $C_1$–$C_4$ alkyl or $C_1$–$C_3$ alkoxy.

8. A method of claim 7 wherein the compound is N-methyl-3-phenyl-4-(4-trifluoromethylphenyl)butanamine, or a pharmaceutically acceptable acid addition salt thereof.

9. A method of claim 7 wherein the compound is N-methyl-3-phenyl-4-(2-methylphenyl)butanamine, or a pharmaceutically acceptable acid addition salt thereof.

10. A method for inhibiting norepinephrine uptake in mammals which comprises administering to a mammal requiring increased neurotransmission of norepinephrine a pharmaceutically effective amount of a compound of claim 1.

11. A method of claim 10 wherein $R^1$ is methyl, $R^2$, $R^3$, $R^4$, and $R^5$ are each hydrogen, and $R^6$ is either trifluoromethyl, $C_1$–$C_4$ alkyl or $C_1$–$C_3$ alkoxy.

12. A method of claim 11 wherein the compound is N-methyl-3-phenyl-4-(2-methylphenyl)butanamine, or a pharmaceutically acceptable acid addition salt thereof.

13. A method of claim 11 wherein the compound is N-methyl-3-phenyl-4-(4-trifluoromethylphenyl)butanamine, or a pharmaceutically acceptable acid addition salt thereof.

14. A method of treating depression in humans comprising administering to a human suffering from depression an effective antidepressant dose of a compound of claim 1.

15. A method of claim 14 wherein the compound is N-methyl-3-phenyl-4-(4-trifluoromethylphenyl)butanamine, or a pharmaceutically acceptable acid addition salt thereof.

16. A method of claim 14 wherein the compound is N-methyl-3-phenyl-4-(2-methylphenyl)butanamine, or a pharmaceutically acceptable acid addition salt thereof.

17. A method of treating anxiety in a human comprising administering to a human suffering from anxiety an effective antianxiety dose of a compound of claim 1.

18. A method of claim 17 wherein the compound is N-methyl-3-phenyl-4-(4-trifluoromethylphenyl)butanamine, or a pharmaceutically acceptable acid addition salt thereof.

19. A method of claim 17 wherein the compound is N-methyl-3-phenyl-4-(2-methylphenyl)butanamine, or a pharmaceutically acceptable acid addition salt thereof.

20. A method of treating obesity in humans comprising administering to a human suffering from obesity an effective antiobesity dose of a compound of claim 1.

21. A method of claim 20 wherein the compound is N-methyl-3-phenyl-4-(4-trifluoromethylphenyl)butanamine, or a pharmaceutically acceptable acid addition salt thereof.

22. A method of claim 20 wherein the compound is N-methyl-3-phenyl-4-(2-methylphenyl)butanamine, or a pharmaceutically acceptable acid addition salt thereof.

23. A method of suppressing the desire of humans to smoke comprising administering to a human in need of such suppression an effective dose to relieve the desire to smoke of a compound of claim 1.

24. A method of claim 23 wherein the compound is N-methyl-3-phenyl-4-(4-trifluoromethylphenyl)butanamine, or a pharmaceutically acceptable acid addition salt thereof.

25. A method of claim 23 wherein the compound is N-methyl-3-phenyl-4-(2-methylphenyl)butanamine, or a pharmaceutically acceptable acid addition salt thereof.

26. A method of suppressing the desire of humans to consume alcohol comprising administering to a human in need of such suppression an effective dose to relieve the desire to consume alcohol of a compound of claim 1.

27. A method of claim 26 wherein the compound is N-methyl-3-phenyl-4-(4-trifluoromethylphenyl)butanamine, or a pharmaceutically acceptable acid addition salt thereof.

28. A method of claim 26 wherein the compound is N-methyl-3-phenyl-4-(2-methylphenyl)butanamine, or a pharmaceutically acceptable acid addition salt thereof.

29. A pharmaceutical formulation comprising a compound of claim 1 and a pharmaceutically acceptable carrier, diluent or excipient therefor.

30. A formulation of claim 29 wherein $R^1$ is methyl, $R^2$, $R^3$, $R^4$, and $R^5$ are each hydrogen, and $R^6$ is either trifluoromethyl, $C_1$–$C_4$ alkyl or $C_1$–$C_3$ alkoxy.

31. A formulation of claim 30 wherein the compound is N-methyl-3-phenyl-4-(4-trifluoromethylphenyl)butanamine, or a pharmaceutically acceptable acid addition salt thereof.

32. A formulation of claim 30 wherein the compound is N-methyl-3-phenyl-4-(2-methylphenyl)butanamine, or a pharmaceutically acceptable acid addition salt thereof.

* * * * *

UNITED STATES PATENT AND TRADEMARK OFFICE
CERTIFICATE OF CORRECTION

PATENT NO. : 4,996,235

DATED : February 26, 1991

INVENTOR(S) : David W. Robertson et al.

It is certified that error appears in the above-identified patent and that said Letters Patent is hereby corrected as shown below:

Column 20:
Claim 1, line 52 - " $_1-C_3$ " should be -- $C_1-C_3$ --.

Signed and Sealed this

Seventeenth Day of November, 1992

Attest:

DOUGLAS B. COMER

Attesting Officer    Acting Commissioner of Patents and Trademarks